(12) United States Patent
Qian et al.

(10) Patent No.: US 12,127,800 B2
(45) Date of Patent: Oct. 29, 2024

(54) INSTRUMENT-BASED REGISTRATION AND ALIGNMENT FOR AUGMENTED REALITY ENVIRONMENTS

(71) Applicant: Medivis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/502,030

(22) Filed: Oct. 14, 2021

(65) Prior Publication Data

US 2022/0218420 A1    Jul. 14, 2022

Related U.S. Application Data

(63) Continuation of application No. 17/148,522, filed on Jan. 13, 2021, now Pat. No. 11,172,996.

(51) Int. Cl.
| | |
|---|---|
| *G06T 19/00* | (2011.01) |
| *A61B 34/00* | (2016.01) |
| *A61B 34/20* | (2016.01) |
| *G06T 19/20* | (2011.01) |

(52) U.S. Cl.
CPC .............. *A61B 34/20* (2016.02); *A61B 34/25* (2016.02); *G06T 19/006* (2013.01); *G06T 19/20* (2013.01); *A61B 2034/2068* (2016.02)

(58) Field of Classification Search
None
See application file for complete search history.

(56) References Cited

U.S. PATENT DOCUMENTS

| | | | |
|---|---|---|---|
| 10,326,975 B2* | 6/2019 | Casas | G06F 3/0304 |
| 2008/0228064 A1* | 9/2008 | Krueger | G01R 33/286 |
| | | | 600/414 |
| 2010/0002921 A1 | 1/2010 | Fenchel | |
| 2018/0193097 A1 | 7/2018 | McLachlin et al. | |
| 2018/0253856 A1 | 9/2018 | Price et al. | |
| 2020/0005486 A1* | 1/2020 | Sinha | G06T 7/337 |
| 2020/0352655 A1* | 11/2020 | Freese | G06T 11/00 |

* cited by examiner

*Primary Examiner* — Saptarshi Mazumder
(74) *Attorney, Agent, or Firm* — Cognition IP, P.C.; Edward Steakley; Rajesh Fotedar (57) ABSTRACT

Various embodiments of an apparatus, methods, systems and computer program products described herein are directed to Registration Engine. The Registration Engine tracks positions of a fiducial marker relative to positions of an Augmented Reality (AR) headset device worn by a user. The Registration Engine receives respective registration landmarks that correspond with locations of a physical region of a patient's anatomy and the tracked positions of the fiducial marker. The Registration Engine generates an AR display of medical data at the AR headset device in alignment with the physical region of a patient's anatomy that corresponds with the respective registration landmarks.

20 Claims, 11 Drawing Sheets

INSTRUMENT-BASED REGISTRATION AND ALIGNMENT FOR AUGMENTED REALITY ENVIRONMENTS

CROSS REFERENCE TO RELATED APPLICATIONS

This application is a continuation of U.S. patent application Ser. No. 17/148,522 entitled "Instrument-Based Registration and Alignment for Augmented Reality Environments," filed on Jan. 13, 2021, the entirety of which is incorporated by reference.

BACKGROUND

Current conventional systems have limitations with regard to two-dimensional (2D) and three-dimensional (3D) images in surgical settings. Surgical planning is necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Various embodiments of an apparatus, methods, systems and computer program products described herein are directed to a Registration Engine. According to various embodiments, The Registration Engine tracks positions of a tip of a localizing instrument relative to various positions of an Augmented Reality (AR) headset device worn by a user, via a fiducial marker. The Registration Engine receives respective registration landmarks that correspond with locations of a physical region of a patient's anatomy identified by the tip of localizing instrument and selection of representations of the physical locations in 3D digital medical data. The landmarks may be physical locations on a patient's body and virtual landmarks of locations on displayed medical data. The Registration Engine generates an AR display of the medical data at the AR headset device in alignment with the physical anatomical region at which the selected physical registration landmarks are situated.

Various embodiments include a module(s) and/or one or more functionalities to redact privacy information/data (such as medical data), to encrypt information/data and to anonymize data to ensure the confidentiality and security of user, patient and system information/data as well as compliance with medical regulatory and privacy law(s) in the United State and/or international jurisdictions.

According to various embodiments, the AR headset device calculates spatial transformations relative to a pre-defined fixed reference point in three-dimensional (3D) space external to the AR headset device in order to determine the coordinates of the tip of the localizing instrument. The coordinates represent the tip's position in that same 3D space external to the AR headset device.

According to various embodiments, the user may touch locations on a patient's body with the tip of the localizing instrument and register the tip's locations as physical landmarks on the patient's body while the tip is in contact with the patient's body. The user may select representations of the physical locations portrayed in displayed medical data (such as a CT scan, an M.R.I.)—and also register the selected display locations as virtual landmarks.

According to various embodiments, the AR headset device presents, in the user's field of vision, a stationary visualization of medical data overlayed upon a corresponding physical region of the patient's anatomy. The Registration Engine identifies portions of a three-dimensional (3D) model of medical data that are currently in a perspective view of the AR headset device. The portions of the 3D model are determined according to device pose data and the virtual landmarks selected by the user.

One or more base images are generated by the Registration Engine based on the identified portions of the 3D model of medical data and sent to the AR headset device. The AR headset device populates the stationary visualization of medical data with a rendering derived from the base images.

According to various embodiments, the user may manipulate (i.e. move, adjust, rotate) the visualization of the medical data overlayed upon the patient and the Registration Engine may apply fine tuning of the visualization of the medical data. The Registration Engine scales down (i.e. minimize) the extent of the graphical modification of the visualization of the medical data resulting from the user's manipulation.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

Figure 1A:
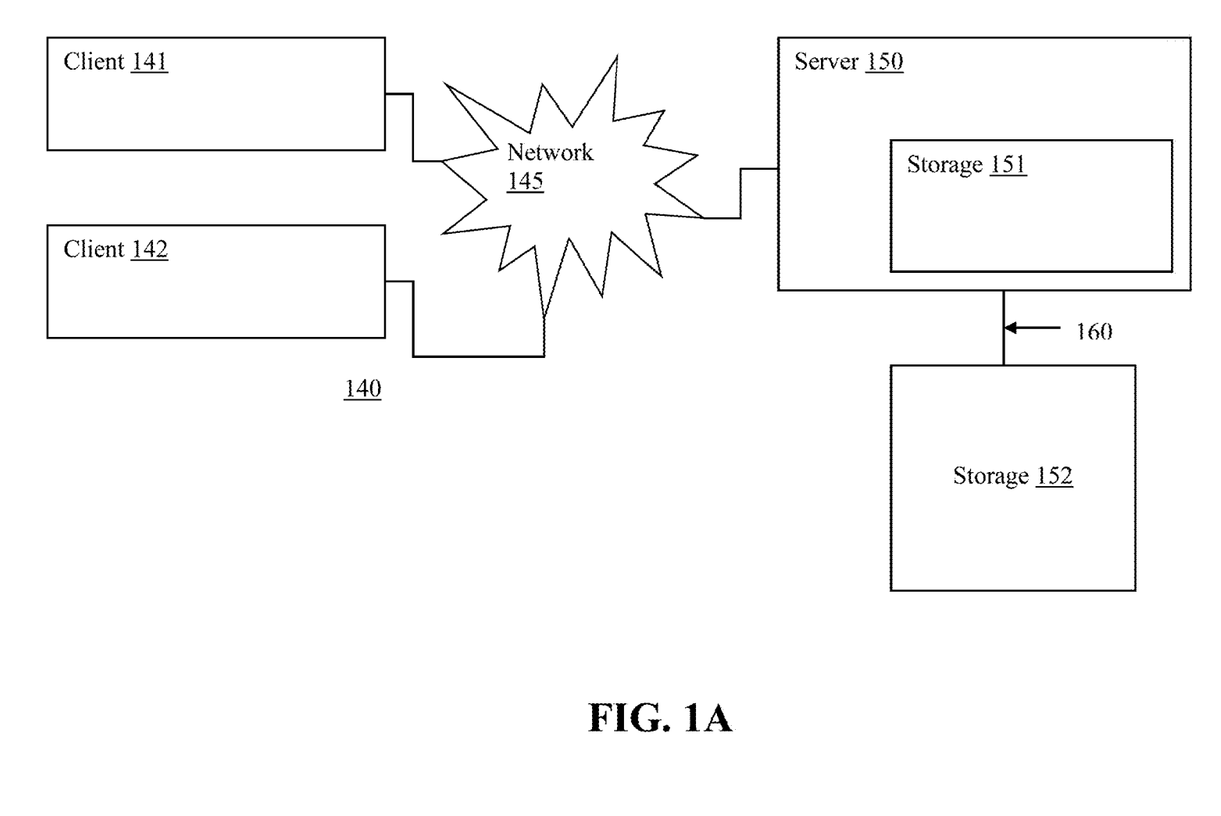
FIG. 1A is a diagram illustrating an exemplary environment in which some embodiments may operate.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

Figure 2:
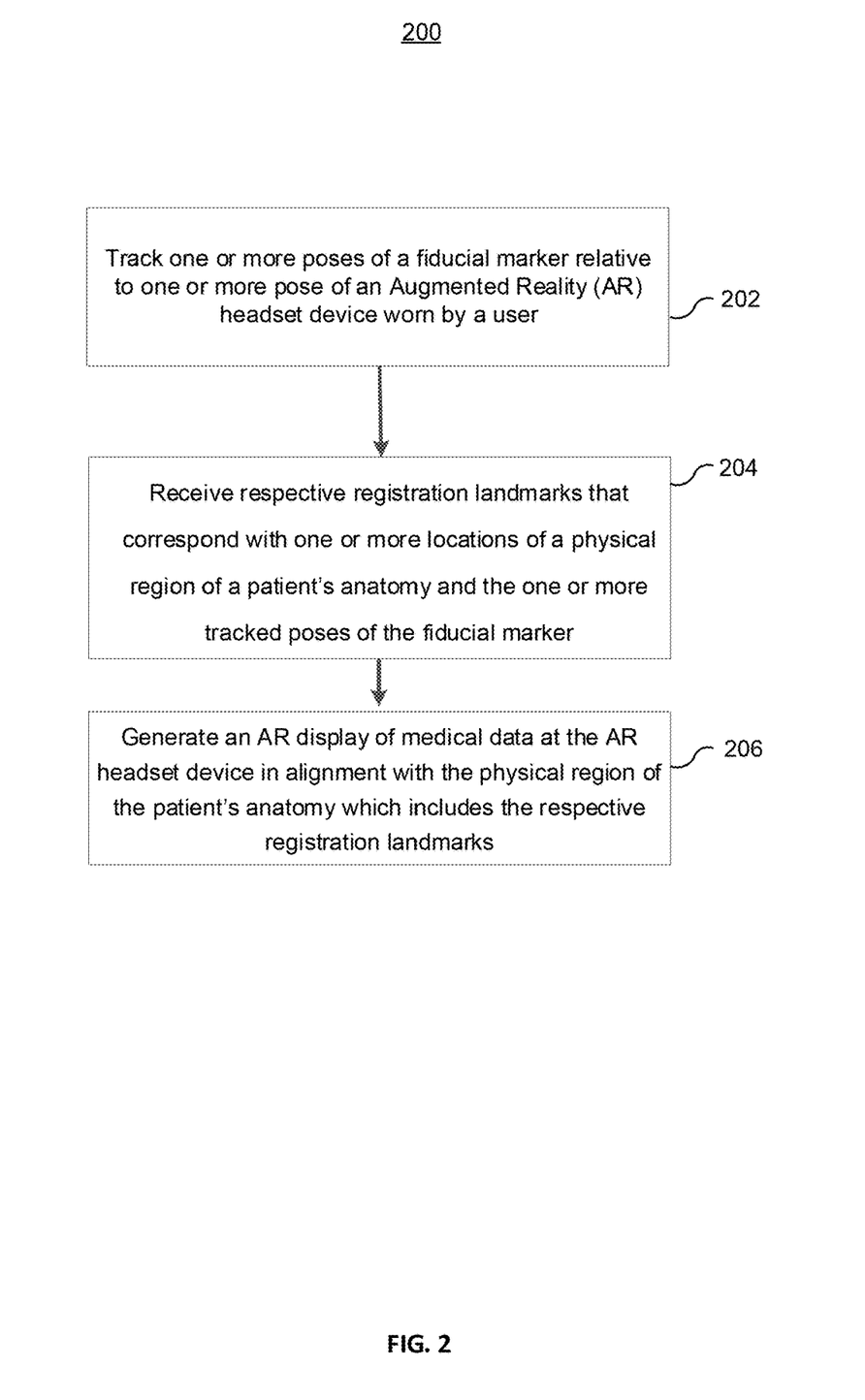
FIG. 2 is a diagram illustrating an exemplary method that may be performed in some embodiments.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
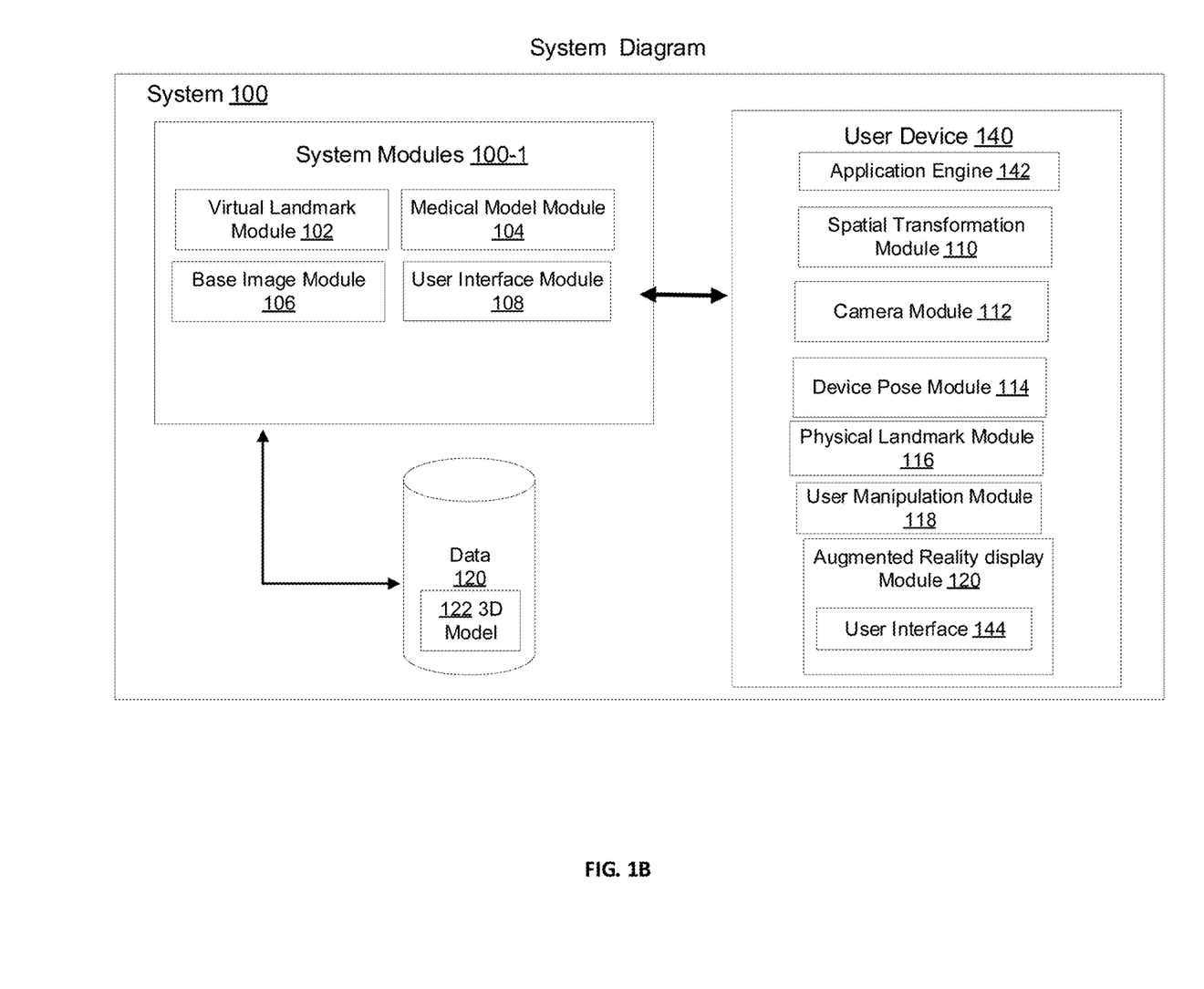
FIG. 1B is a diagram illustrating an exemplary environment in which some embodiments may operate.

FIG. 1B illustrates a block diagram of an example system 100 for various embodiments that includes system modules 100-1, such as: a virtual landmark module 102, a medical model module 104, a base image module 106 and a user interface module 108.

The system 100 also includes one or more user devices 140 (such as one or more Augmented Reality headset devices) to display output, via a user interface 144 generated by an application engine 142. The user device includes: a spatial transformation module 110, a camera module 112, a device pose module 114, a physical landmark module 116, a user manipulation module 116 and an augmented reality display module 118. It is understood that the user device(s) 140 may further include one or more of the modules 102, 104, 106, 108 or respective portions of the modules 102 . . . . 118 may be distributed and implemented amongst a plurality of user devices 140 and one or more workstations.

The virtual landmark module 102 of the system 100 may perform functionality as illustrated in FIGS. 2, 3, 4A, 4B, 5A, 5B, 5C and 6 ("2-6").

The medical model module 104 of the system 100 may perform functionality as illustrated in FIGS. 2-6.

The base image module 106 of the system 100 may perform functionality illustrated in FIGS. 2-6.

The user interface module 108 of the system 100 may perform functionality illustrated in FIGS. 2-6.

The spatial transformation module 110 of the system 100 may perform functionality as illustrated in FIGS. 2-6.

The camera module 112 of the system 100 may perform functionality as illustrated in FIGS. 2-6.

The device pose module 114 of the system 100 may perform functionality as illustrated in FIGS. 2-6.

The physical landmark module 116 of the system 100 may display information based on functionality as illustrated in FIGS. 2-6.

The user manipulation module 118 of the system 100 may perform functionality as illustrated in FIGS. 2-6.

The augmented reality display module 120 of the system 100 may perform functionality as illustrated in FIGS. 2-6.

Any module or component of the system 100 may have access to a 3D model of medical data 122 or may have one or more portions of the 3D model 122 stored locally. While the databases(s) 120 is displayed separately, the databases and information maintained in a database may be combined together or further separated in a manner the promotes retrieval and storage efficiency and/or data security.

As shown in flowchart 200 of FIG. 2, the Registration Engine includes the Augmented Reality (AR) headset device worn by a user which tracks one or more poses of a fiducial marker relative to one or more poses of the AR headset device (Act 202). In various embodiments, a camera(s) disposed on the AR headset device captures one or more images as the AR headset device moves. The AR headset device calculates a first spatial transformation based on the captured image(s) and a predefined fixed reference point in three-dimensional (3D) space external to the AR headset device. The predefined fixed reference point represents a position in the physical world according to x, y and z coordinates. According to various embodiments, the AR headset device executes one or more simultaneous localization and mapping (SLAM) algorithms based on image input from the camera and sensor inputs. For example, sensor inputs may be data from a gyroscope or accelerometer disposed on the AR headset device. The SLAM algorithm(s) generate device pose data representing a physical orientation and a position of the AR headset device relative to the predefined fixed reference point. According to various embodiments, pose data of an instrument, fiducial marker, and/or a headset device represents a physical orientation in a 3D space defined by a unified coordinate system.

In various embodiments, the camera(s) of the AR headset device captures one or more images of the fiducial marker as the fiducial marker moves. The AR headset device calculates a second spatial transformation based on the captured images(s) of the fiducial marker and camera data. For example, camera data may be one or more of focal length, distortion, etc. The second spatial transformation may be calculated according to one or more fiducial tracking algorithms executed at the AR headset device. The AR headset device generates respective coordinates representing the physical orientations and positions of the fiducial marker in the 3D space relative to the predefined fixed reference point. In some embodiments, a fiducial marker may be an infrared marker tracked by an infrared (stereo) camera(s), or an electromagnetic marker tracked by an electromagnetic sensor(s).

In various embodiments, the AR headset device calculates a third spatial transformation based on a fixed distance of a localizing instrument ("instrument") between the fiducial marker and a tip of the instrument. Since the tip of the instrument will always be situated at a fixed distance away from the fiducial marker on the same instrument, the respective coordinates for the fiducial marker calculated by the second special transformation can be utilized along with the fixed distance to generate respective coordinates representing one or more physical orientations and positions of tip of the instrument in the 3D space relative to the predefined fixed reference point.

The Registration Engine receives respective registration landmarks that correspond with one or more locations of a physical region of a patient's anatomy identified by the coordinates of the one or more tracked poses of the fiducial marker (Act 204). In various embodiments, the Registration Engine receives one or more physical landmark registration notifications from the user indicating that particular coordinates of the tip of the instrument (determined by the third spatial transformation) represent the locations of respective physical landmarks at a region of the patient's anatomy. For example, the user may touch various locations on a patient's abdomen with the instrument's tip. After each touch, the user may trigger a selection functionality that selects the touched location and triggers a notification that the currently touched location of the patient's abdomen is to be registered as a physical landmark and represented by the current coordinates of the instrument's tip. Once registered as a physical landmark, the Registration Engine stores the current coordinates of the tip of the instrument when the user triggered the selection functionality. By storing a registered physical landmark according to the tip's coordinates, the Registration Engine acquires data that represents a position of a location of the patient's anatomy in the 3D space relative to the predefined fixed reference point.

In various embodiments, the Registration Engine receives one or more virtual landmark registration notifications from the user that one or more particular locations on a display of medical data associated with the region of the patient's anatomy correspond to the one or more respective physical landmarks. For example, a workstation(s) may display medical data, such as a CT scan or MRI of the patient's abdomen. The user may select locations of the display that correspond to the physical landmarks on the patient's abdomen. For example, the user may touch various locations of a displayed CT scan of patient's abdomen that are the same locations selected as the physical landmarks. Again, after each touch on the displayed scan, the user may trigger a selection functionality that selects the touched display location and triggers a notification that the currently touched display location is to be registered as a virtual landmark. In some embodiments, the Registration Engine may implement an iterative closest point algorithm(s) for identification of select virtual landmarks.

The Registration Engine includes the AR headset device generating an AR display of medical data in alignment with the respective registration landmarks which includes the respective registration landmarks (Act 206). According to various embodiments, the AR headset device generates a first AR display based on medical data related to a physical region of the patient's anatomy. The AR headset device presents, in the user's field of vision, a stationary visualization of the medical data overlayed upon the physical region of the patient's anatomy.

Figure 3:
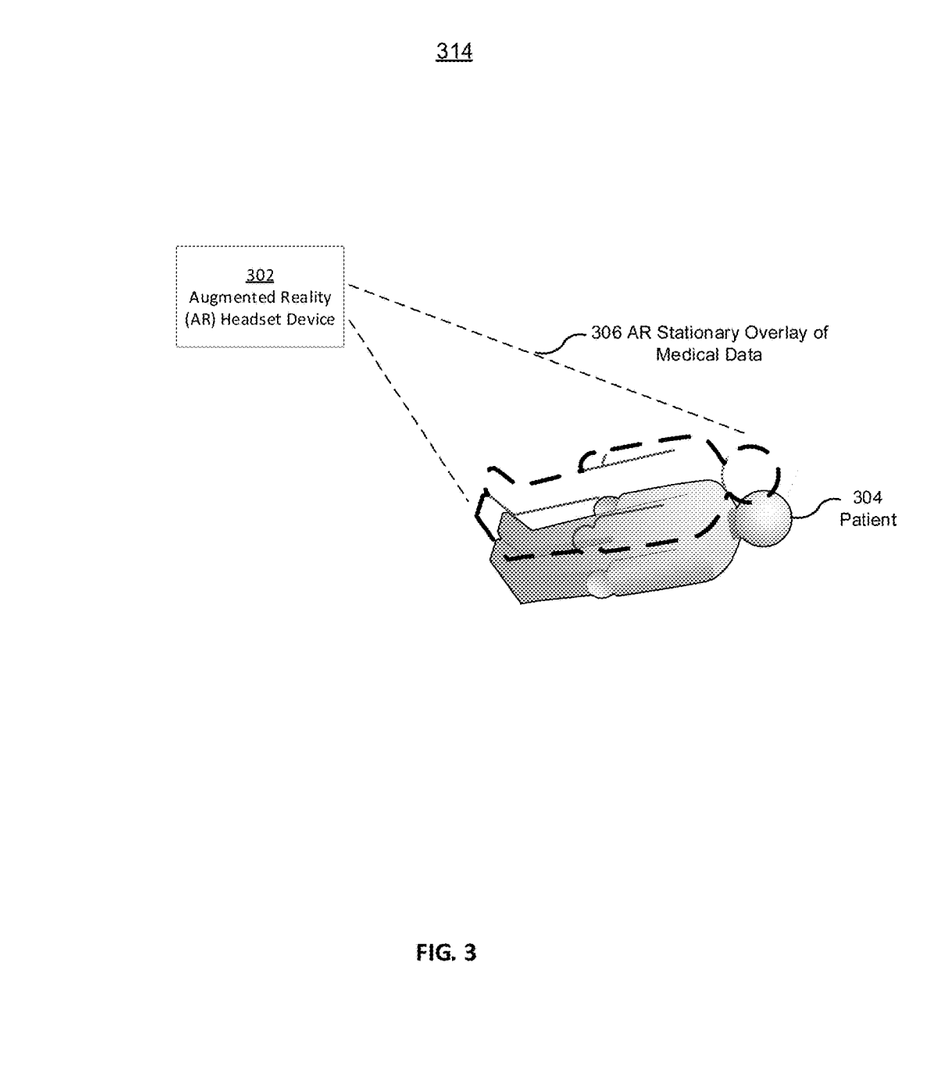
FIG. 3 is a diagram illustrating an exemplary environment in which some embodiments may operate.

As shown in diagram 300 of FIG. 3, the AR headset device 302 may be worn by a user physically situated in proximity to a patient 304. The AR headset device 302 generates an AR display to be viewed by the user as the user moves around the patient and changes the position(s) of the AR headset device 302 as result of the user's head movements. As the position of the AR headset device 302 continually changes, the AR headset device 302 maintains a stationary AR display of medical data 306 so that the overlay 306 is continually displayed in alignment with registered physical landmarks on the patient's anatomy regardless of where the user moves.

Figure 4A:
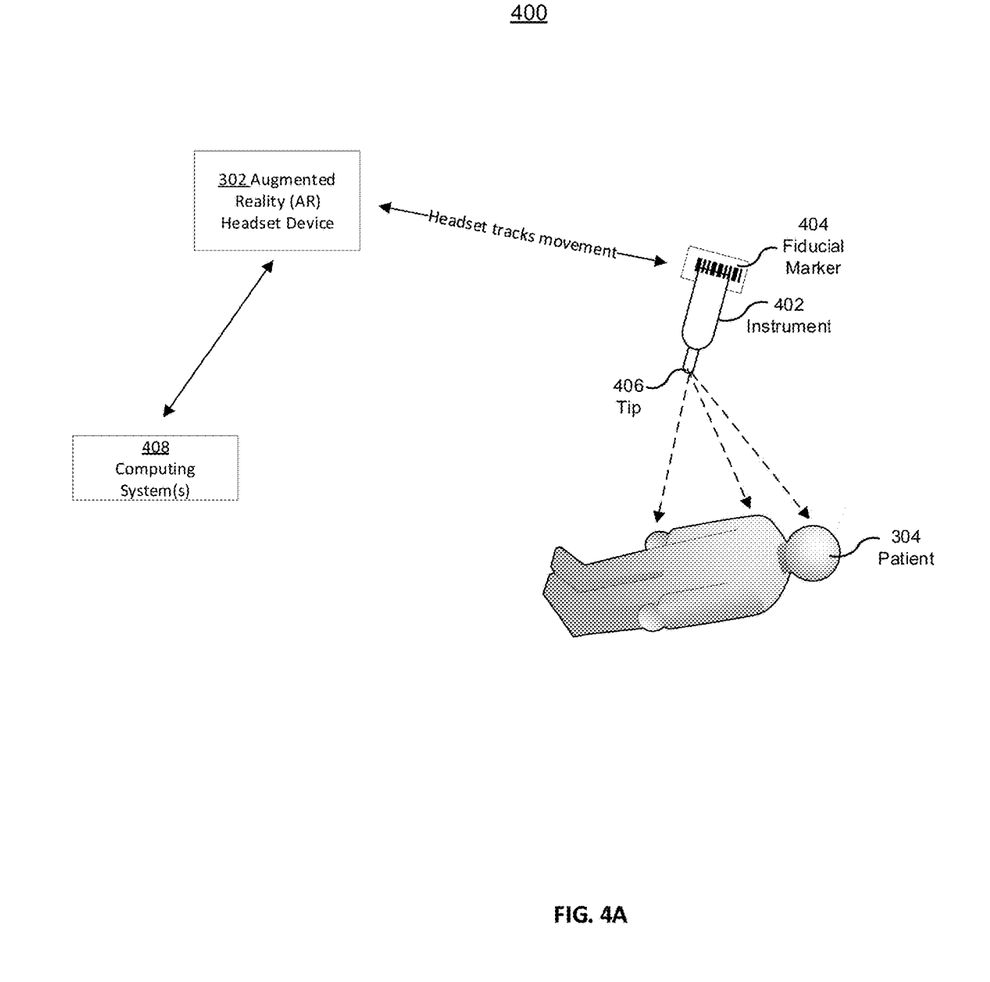
FIGS. 4A and 4B are each a diagram illustrating an exemplary environment in which some embodiments may operate.

As shown in diagram 400 of FIG. 4A, a localizing instrument(s) 402 may be held by the user. The instrument 402 includes a fiducial marker 404 at a permanent location at the instrument 402. For example, the fiducial marker 404 may be affixed to the instrument 402. In various embodiments, the fiducial marker 404 may be a graphic(s) and/or a symbol(s) that is perceptible to a camera(s) disposed on the AR headset device 302. For example, the fiducial marker 404 may be a quick response (QR) code. Since the instrument 402 is a physical object, it has a tip 406. The location of the tip 406 on the instrument will be extended from the fiducial marker 404 on the instrument 402 according to a permanent, fixed distance. A computing system(s) 408 is further included in Registration Engine to provide a 3D model of medical data based on patient data. For example, the patient data may be a computerized tomography (CT) scan or a magnetic resonance image (MM). The 3D model may be derived from one or more portions of the patient data. The computing system(s) 408 sends base image data of various portions of the 3D model to the headset device 302 for rendering as the overlay of medical data 306.

The AR headset device 302 includes a camera(s) which is implemented as, in part, a tracking unit in order to identify physical landmarks on the patient's anatomy. In various embodiments, the user wearing the AR headset device 302 may hold the instrument 402 and select specific locations on the anatomy of the patient with the tip 406 of the instrument 402 in order to register the specific locations are respective physical landmarks. The Registration Engine stores the registered physical landmarks according to the coordinates of the tip of the instrument 402 when the user touched each physical landmark on the patient's anatomy with the instrument's tip.

Figure 4B:
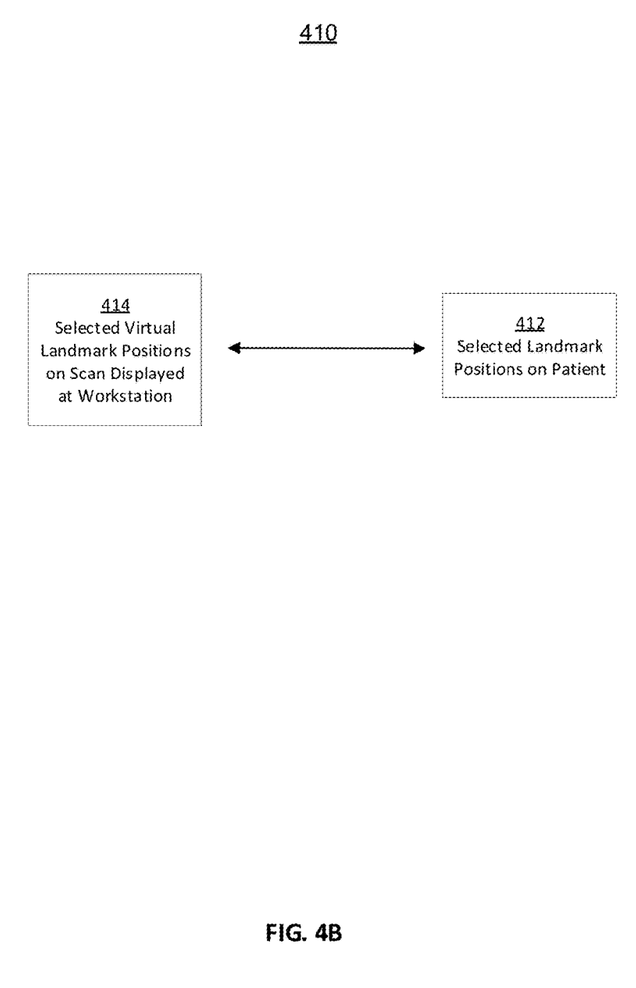

As shown in diagram 410 of FIG. 4B, the Registration Engine defines the selected locations on the patient's anatomy as respective registered physical landmarks 412. The user further selects representations of the registered physical locations 412 portrayed in a display of medical data at a computing system(s) 408. For example, a workstation(s) may display a CT scan of a part of the patient's anatomy where the user has selected the respective physical landmarks 412. The user may select locations within the display that correspond to the registered physical locations 412. The Registration Engine defines the selected locations on the displayed medical data as respective virtual landmarks 414.

For example, if the user touches the tip of the instrument to the patient's earlobe and registers the tip's current coordinates are representing a location of a physical landmark, the user may then access a displayed medical scan of the patient's ear and select a location on the displayed scan that represents the same location as the registered physical landmark on the ear lobe. The selected location on the displayed scan is defined by the Registration Engine as a virtual landmark. In some embodiments, one or more virtual landmarks 414 may be registered before one or more physical landmarks 412. In some embodiments, one or more physical landmarks 412 may be registered before one or more virtual landmarks 414. In some embodiments, the user may alternate between selecting and registration of physical landmarks 412 and virtual landmarks 414.

Figure 5A:
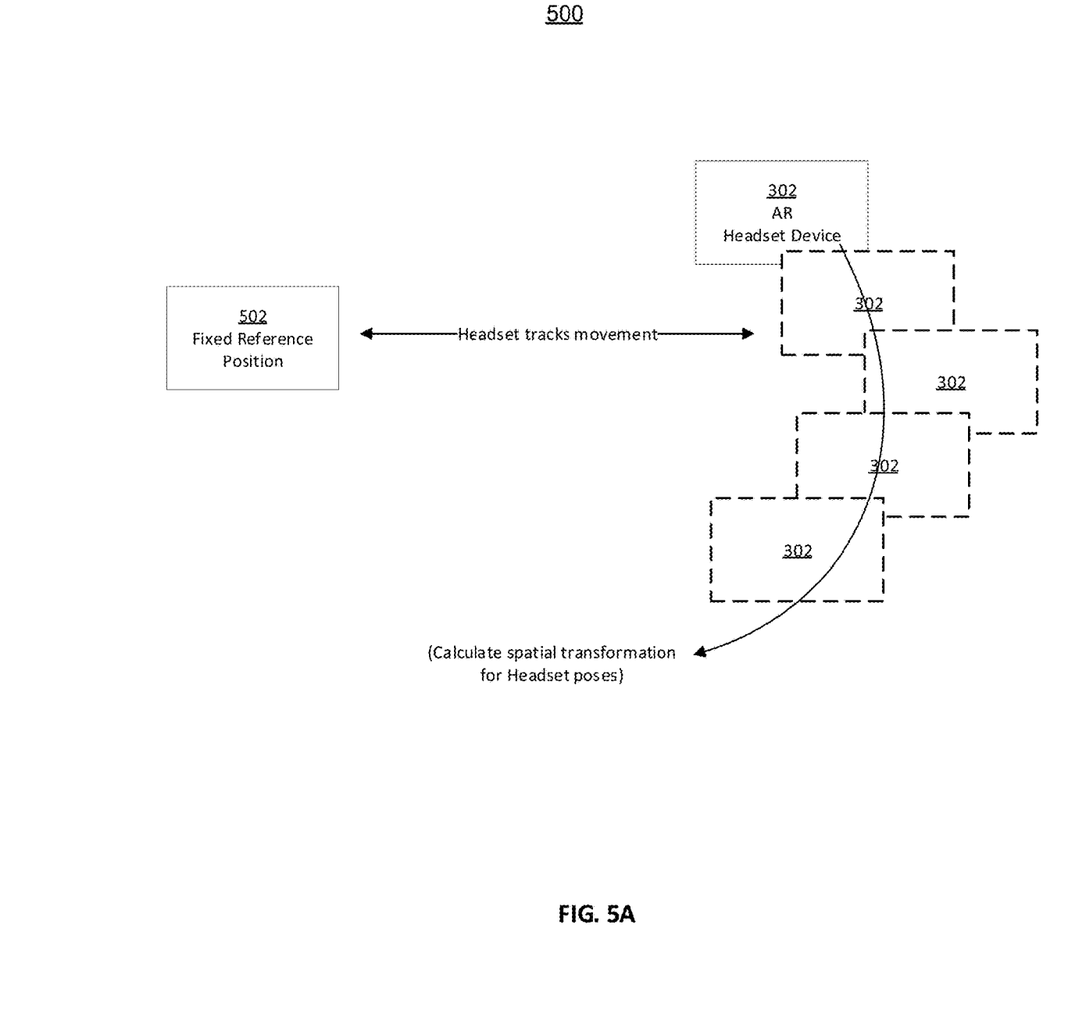
FIGS. 5A, 5B and 5C are each a diagram illustrating an exemplary environment in which some embodiments may operate.

As shown in diagram 500 of FIG. 5A, the Registration Engine defines a fixed reference position 502 in the physical world according to x, y and z coordinates of a 3D space. The fixed reference position 502 is external to the headset device 302. In some embodiments, the fixed reference position 502 may be arbitrary x, y and z coordinates with respect to the headset device 302. The headset device 302 continually tracks its own pose(s) with reference to the fixed reference position 502. The headset device 302 generates device pose data resulting from calculating a spatial transformation(s) to determine the device's 302 current physical orientation(s) and position(s). The AR headset device 302 continually sends the device pose data to the workstation(s) and the workstation(s) continually generates base images of portions of a 3D model of medical data that correspond to the received instances of device pose data.

Figure 5B:
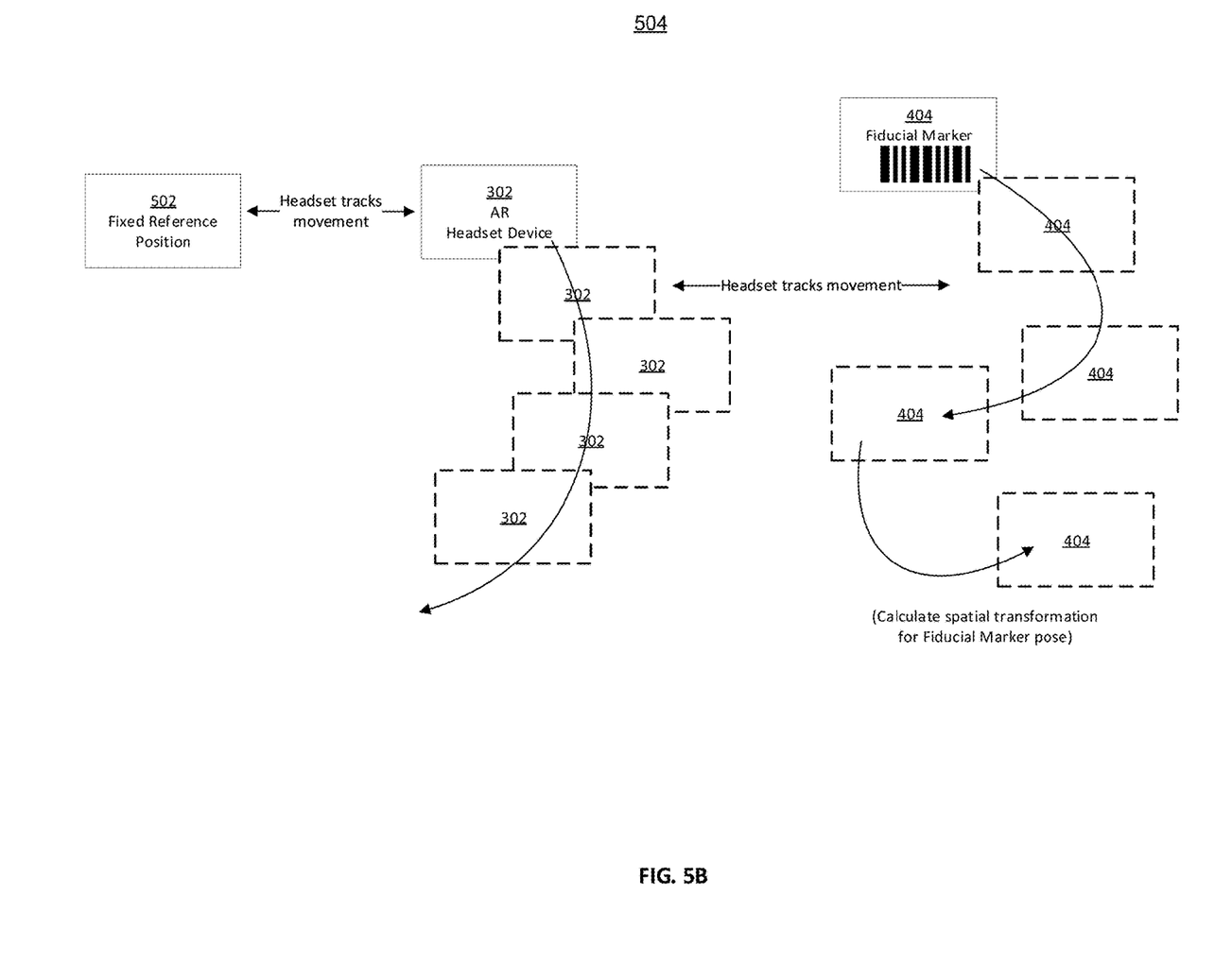

As shown in diagram 504 of FIG. 5B, as the user wearing the headset device 302 manipulates the instrument 402 and as the instrument 402 moves and changes locations, the camera(s) of the headset device 302 captures image data of the fiducial marker 404 on the instrument 402 moving through physical space. As the headset device 302 continually generates device pose data based on its own pose relative to the fixed reference position 502, the headset device 302 further continually generates fiducial marker pose data relative to the device pose data. For example, the headset device 302 generates the fiducial marker pose data resulting from calculating a spatial transformation(s) to determine the fiducial marker's 404 current physical orientation(s) and position(s).

Figure 5C:
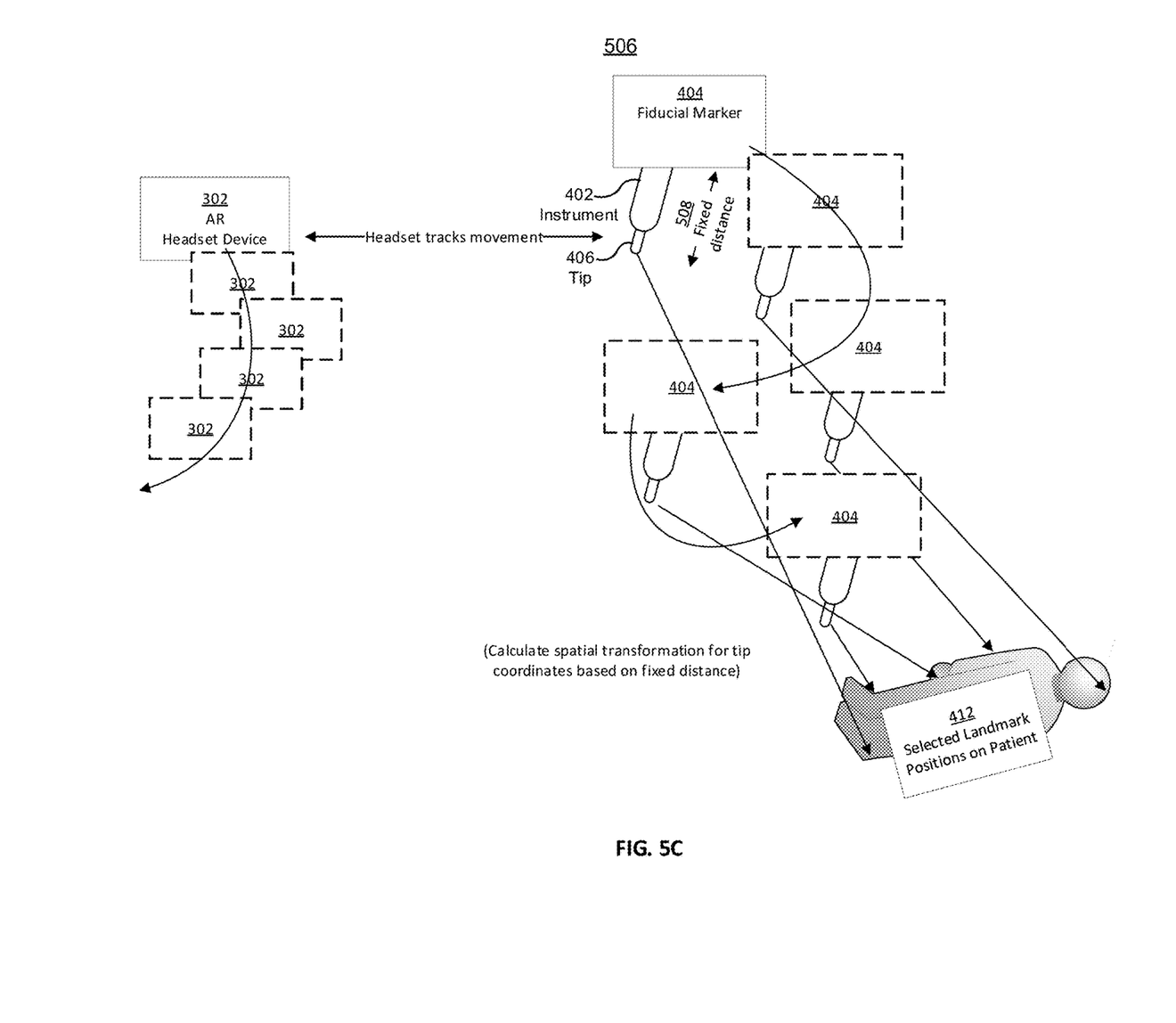

As shown in diagram 506 of FIG. 5C, the instrument 402 has a tip 406 that extends from the fiducial marker 404 on the instrument 402 according to a fixed distance 508. Wherever the instrument 402 is moved and positioned by the user, the fiducial marker 404 will be tracked by the headset device 302 to generate the fiducial marker pose data. Each instance of fiducial marker pose data represents the fiducial marker's placement in the physical world relative to the headset device 302 and the fixed reference point 502. The headset device 302 further calculates another spatial transformation with respect to the fiducial marker pose data and the fixed distance on the instrument 402 between the fiducial marker 404 and the tip 406 in order to determine the tip's 406 placement in the physical world. As the user places the tip 406 at a particular location on the patient's anatomy, the user notifies the Registration Engine that the current placement (i.e. current coordinates) of the tip 406 corresponds to that particular location on the patient's anatomy. The Registration Engine records the current coordinates of the tip 406 as registration of a particular physical landmark.

Figure 6:
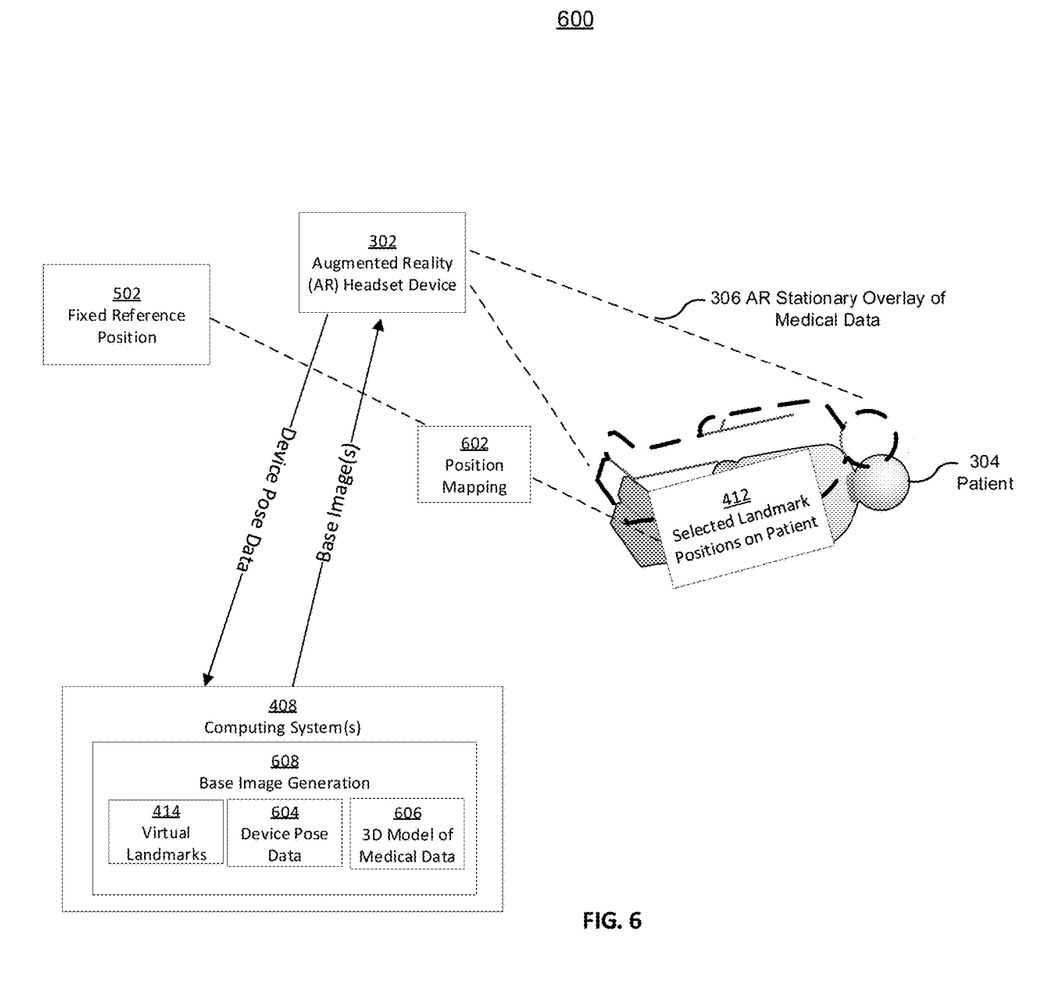
FIG. 6 is a diagram illustrating an exemplary environment in which some embodiments may operate.

As shown in diagram 600 of FIG. 6, the spatial transformations calculated by the AR headset device 302 identify coordinates of physical landmarks 412 on a patient 304 relative to a fixed reference position 503 in 3D space. As such, the spatial transformations calculated at the AR headset device 302 generate a mapping 602 between the fixed reference position 502 and each of the registered physical landmarks 412.

As the user (and the AR headset device 302) move, the AR headset device 302 will continually generate and update display of an overlay 306 in order to maintain a visual appearance to the user that the overlay 306 is stationary in the user's field of vision regardless of where the user moves with respect to the patient's 304 current location. However, the visualization of the medical data that populates the stationary overlay 306 will continually change based on one or more base images generated 608 by the computing system(s) 408 received by the AR headset device 302, the device pose data 604 and the respective virtual and physical landmarks 412, 414.

In various embodiments, the computing system(s) 408 of the Registration Engine (for example, a workstation(s)) may access a 3D model 606 of a scan of a portion(s) of the patient's anatomy. The workstation may continually receive instances of device pose data 604 from the AR headset device 302. Based on the received device pose data 604 and the virtual landmarks 414, the workstation identifies portions of the 3D model 606 that are in a current perspective view of the AR headset device 302 as a result of a position of the AR headset device 302 as represented by the device pose data 604. Further, the workstation identifies those portions of the 3D model 606 that are bounded by the virtual landmarks 414.

For example, if the user is currently positioned such that the right side of the patient's head is in view to the user (and the AR headset device 302), the device pose data 604 represents the AR headset device's 302 placement with respect to the right side of the patient's head. Upon receipt of the device pose data 604, the workstation(s) accesses a 3D model 606 based on a CT scan of the patient's head and identifies portions of the 3D model 606 that depict the right side of the patient's head that are bounded by the virtual landmarks 414.

The workstation(s) generates a first base image of the identified portions of the right side of the patient's 304 head and sends the first base image to the AR headset device 302. The AR headset device 302 renders a visualization of the first base image for the stationary overlay 306 in alignment with the patient's head. As the user's moves, updated device pose data is sent from the AR headset device 302 to the workstation(s) and the workstation(s) identifies different portions of the 3D model 606 that are now in an updated perspective view of the AR headset device 302 as represented by the updated device pose data. The workstation(s) generates a second base image of the different portions of the 3D model 606 and sends the second base image to the AR headset device 302. The AR headset device 302 then renders an updated visualization based on the second base image in the stationary overlay 306.

According to various embodiments, it is understood that the Registration Engine can be implemented by one or more workstations. In other embodiments, it is understood that the RegistrationRengine can be implemented on an AR headset device that stores medical model data (e.g. 3D model 606) locally on the AR headset device itself.

According to various embodiments, one or more virtual landmarks can be registered by the Registration Engine in response to the user performing a hand gesture interaction(s) with respect to a portion of medical data displayed on an AR interface of the AR headset device.

Figure 7:
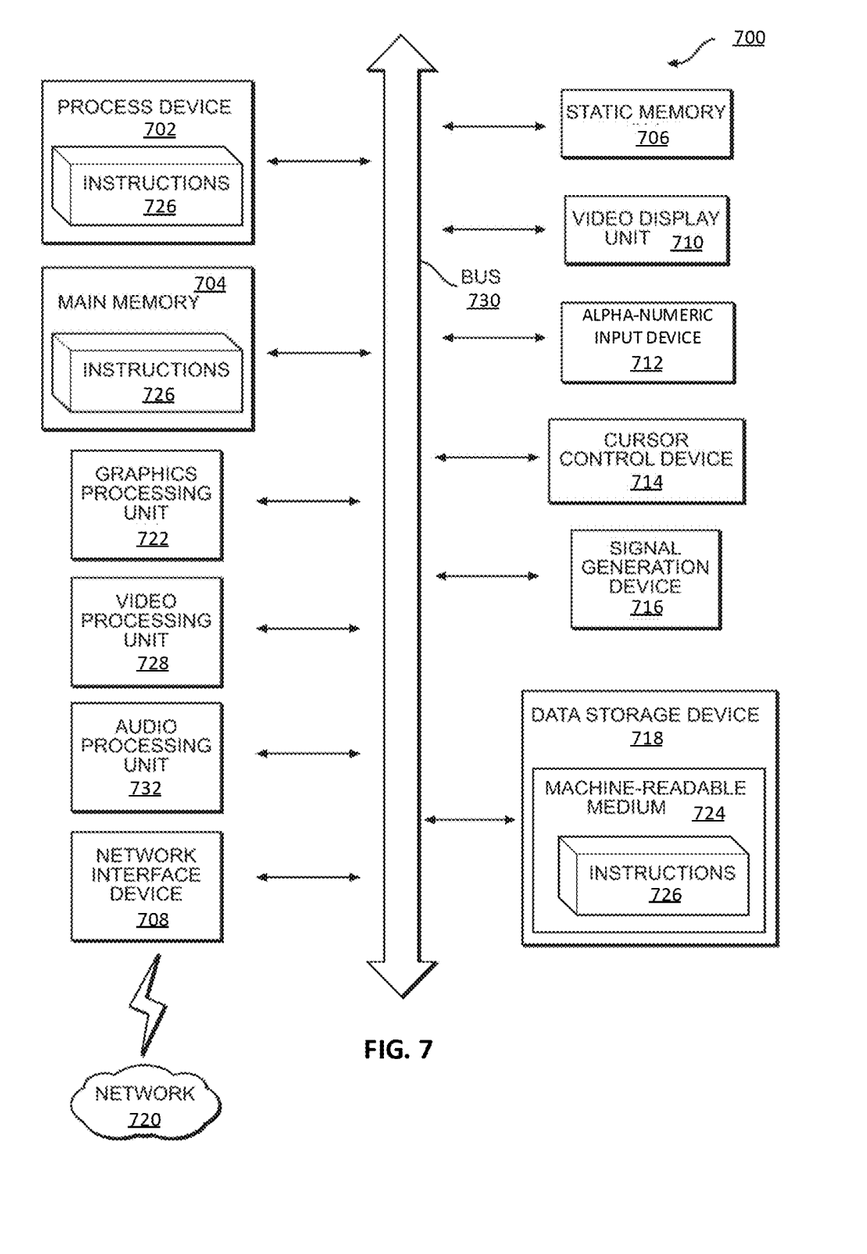
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
    tracking one or more positions and orientations of a fiducial marker, disposed on an instrument at a distance from a tip of the instrument, relative to one or more positions and orientations of an Augmented Reality (AR) headset device;
    receiving one or more instances of respective types of landmark registration notifications with respect to at least one anatomical region of a patient's anatomy,
        (a) wherein a first type of landmark registration notification corresponds to a physical landmark registration based on particular coordinates of the tip of the instrument selected in response to contact between the tip and a surface of a physical instance of the anatomical region, the particular coordinates (i) being relative to a predefined fixed reference point in three-dimensional (3D) space external to the AR headset device and (ii) representing a respective physical landmark at the location of contact between the tip and surface;
    storing a plurality of physical landmark registrations each identifying a different set of coordinates selected by respective instances of the tip touching the patient's body;
        (b) wherein a second type of landmark registration notification corresponds to a virtual landmark registration based on selection of a location of a display portraying the anatomical region, the selection of the location identifying medical data and creating an association between the identified medical data with the respective physical landmark at a location of contact between the tip and the surface;
    receiving and storing a plurality of selected locations of the display corresponding to the registered physical landmark locations as a plurality of virtual landmark registrations; and
    generating an AR display of medical data that corresponds with the plurality of physical landmark registrations and the virtual landmark registrations, the AR display of medical data visualized in alignment with the physical instance of the anatomical region;
    generating device pose data corresponding to movement of the AR headset device;
    identifying, based on the device pose data, portions of a 3D model of the anatomical region bounded by the virtual landmark registrations; and
    generating and sending image data of the anatomical region to be rendered for visualization by the AR headset device.

2. The computer-implemented method of claim 1, wherein generating an AR display of medical data comprises:
    generating a first AR display based on the identified medical data, the first AR display comprising a stationary visualization of the identified medical data overlaid upon a physical region of the patient's anatomy.

3. The computer-implemented method of claim 2, wherein generating a first AR display comprises:
    applying a mapping to a model of the medical data related to the physical region of the patient's anatomy, the mapping determined from the predefined fixed reference point in three-dimensional (3D) space to one or more respective physical landmarks selected at the physical region of the patient's anatomy; and
    rendering the identified medical data as the stationary visualization of the medical data overlaid upon the physical region of the patient's anatomy.

4. The computer-implemented method of claim 3, wherein tracking one or more poses of a fiducial marker relative to one or more positions of the Augmented Reality (AR) headset device comprises:
    capturing one or more images via one or more cameras disposed on the AR headset device;
    calculating a first spatial transformation based on the one or more captured images and the predefined fixed reference point in 3D space; and
    generating the device pose data resulting from the spatial transformation, the device pose data representing respective physical orientations and positions of the AR headset device.

5. The computer-implemented method of claim 4, further comprising:
    capturing one or more images of the fiducial marker via the one or more cameras disposed on the AR headset device as the AR headset device changes headset poses and as the instrument moves;

calculating a second spatial transformation based on the one or more captured images via one or more fiducial tracking algorithms executed at the AR headset device; and generating respective coordinates representing one or more physical orientations and positions of the fiducial marker in the 3D space.

6. The computer-implemented method of claim 5, further comprising:

calculating a third spatial transformation based on a fixed distance of the instrument between the fiducial marker and the tip of the instrument; and generating respective coordinates representing one or more physical orientations and positions of tip of the instrument in the 3D space.

7. The computer-implemented method of claim 1, wherein generating an AR display of medical data at the AR headset device comprises:

at one or more computer systems located remotely from the AR headset device:
identifying one or more portions of the medical data, bounded by the virtual landmarks registrations, that correspond to a current view, at the AR headset device, of one or more portions of the physical instance of the anatomical region;
generating one or more AR display base images based on a rendering of the identified medical data and one or more of the bounded portions of the medical data; and
sending the one or more AR display base images to the AR headset device.

8. A system comprising one or more processors, and a non-transitory computer-readable medium including one or more sequences of instructions that, when executed by the one or more processors, cause the system to perform operations comprising:

tracking one or more positions and orientations of a fiducial marker, disposed on an instrument at a distance from a tip of the instrument, relative to one or more positions and orientations of an Augmented Reality (AR) headset device;

receiving one or more instances of respective types of landmark registration notifications with respect to at least one anatomical region of a patient's anatomy,
(a) wherein a first type of landmark registration notification corresponds to a physical landmark registration based on particular coordinates of the tip of the instrument selected in response to contact between the tip and a surface of a physical instance of the anatomical region, the particular coordinates (i) being relative to a predefined fixed reference point in three-dimensional (3D) space external to the AR headset device and (ii) representing a respective physical landmark at the location of contact between the tip and surface;

storing a plurality of physical landmark registrations each identifying a different set of coordinates selected by respective instances of the tip touching the patient's body;
(b) wherein a second type of landmark registration notification corresponds to a virtual landmark registration based on selection of a location of a display portraying the anatomical region, the selection of the location identifying medical data and creating an association between the identified medical data with the respective physical landmark at the location of contact between the tip and the surface;

receiving and storing a plurality of selected locations of the display corresponding to the registered physical landmark locations as a plurality of virtual landmark registrations;

generating an AR display of medical data that corresponds with the plurality of physical landmark registrations and the virtual landmark registrations, the AR display of medical data visualized in alignment with the physical instance of the anatomical region;

generating device pose data corresponding to movement of the AR headset device;

identifying, based on the device pose data, portions of a 3D model of the anatomical region bounded by the virtual landmark registrations; and generating and sending image data of the anatomical region to be rendered for visualization by the AR headset device.

9. The system of claim 8, wherein generating an AR display of medical data comprises:

generating a first AR display based on the identified medical data, the first AR display comprising a stationary visualization of the identified medical data overlaid upon a physical region of the patient's anatomy.

10. The system of claim 9, wherein generating first AR display comprises:

applying a mapping to a model of the medical data related to the physical region of the patient's anatomy, the mapping determined from the predefined fixed reference point in three-dimensional (3D) space to one or more respective physical landmarks selected at the physical region of the patient's anatomy; and
rendering the identified medical data as the stationary visualization of the medical data overlaid upon the physical region of the patient's anatomy.

11. The system of claim 10, wherein tracking one or more poses of a fiducial marker relative to one or more positions of an Augmented Reality (AR) headset device comprises:

capturing one or more images via one or more cameras disposed on the AR headset device;
calculating a first spatial transformation based on the one or more captured images and the predefined fixed reference point in 3D space; and
generating the device pose data resulting from the spatial transformation, the device pose data representing respective physical orientations and positions of the AR headset device.

12. The system of claim 11, further comprising:

capturing one or more images of the fiducial marker via the one or more cameras disposed on the AR headset device as the AR headset device changes headset poses and as the instrument moves;
calculating a second spatial transformation based on the one or more captured images via one or more fiducial tracking algorithms executed at the AR headset device; and
generating respective coordinates representing one or more physical orientations and positions of the fiducial marker in the 3D space.

13. The system of claim 12, further comprising:

calculating a third spatial transformation based on a fixed distance of the instrument between the fiducial marker and the tip of the instrument; and
generating respective coordinates representing one or more physical orientations and positions of tip of the instrument in the 3D space.

14. The system of claim 8, wherein generating an AR display of medical data at the AR headset device comprises:
- at one or more computer systems located remotely from the AR headset device:
  - identifying one or more portions of the medical data, bounded by the virtual landmarks registrations, that correspond to a current view, at the AR headset device, of one or more portions of the physical instance of the anatomical region;
  - generating one or more AR display base images based on a rendering of the identified medical data and one or more of the bounded portions of the medical data; and
  - sending the one or more AR display base images to the AR headset device.

15. A computer program product comprising a non-transitory computer-readable medium having a computer-readable program code embodied therein to be executed by one or more processors, the program code including instructions for:
- tracking one or more positions and orientations of a fiducial marker, disposed on an instrument at a distance from a tip of the instrument, relative to one or more positions and orientations of an Augmented Reality (AR) headset device;
- receiving one or more instances of respective types of landmark registration notifications with respect to at least one anatomical region of a patient's anatomy,
  - (a) wherein a first type of landmark registration notification corresponds to a physical landmark registration based on particular coordinates of the tip of the instrument selected in response to contact between the tip and a surface of a physical instance of the anatomical region, the particular coordinates (i) being relative to a predefined fixed reference point in three-dimensional (3D) space external to the AR headset device and (ii) representing a respective physical landmark at the location of contact between the tip and surface;
  - storing a plurality of physical landmark registrations each identifying a different set of coordinates selected by respective instances of the tip touching the patient's body;
  - (b) wherein a second type of landmark registration notification corresponds to a virtual landmark registration based on selection of a location of a display portraying the anatomical region, the selection of the location identifying medical data and creating an association between the identified medical data with the respective physical landmark at a location of contact between the tip and the surface;
  - receiving and storing a plurality of selected locations of the display corresponding to the registered physical landmark locations as a plurality of virtual landmark registrations; and
    - generating an AR display of medical data that corresponds with of the plurality of physical landmark registrations and the virtual landmark registrations, the AR display of medical data visualized in alignment with the physical instance of the anatomical region;
    - generating device pose data corresponding to movement of the AR headset device;
    - identifying, based on the device pose data, portions of a 3D model of the anatomical region bounded by the virtual landmark registrations; and
    - generating and sending image data of the anatomical region to be rendered for visualization by the AR headset device.

16. The computer program product of claim 15, wherein generating an AR display of medical data comprises:
- generating a first AR display based on the identified medical data, the first AR display comprising a stationary visualization of the identified medical data overlaid upon a physical region of the patient's anatomy.

17. The computer program product of claim 16, wherein generating a first AR display comprises:
- applying a mapping to a model of the medical data related to the physical region of the patient's anatomy, the mapping determined from the predefined fixed reference point in three-dimensional (3D) space to one or more respective physical landmarks selected at the physical region of the patient's anatomy; and
- rendering the identified medical data as the stationary visualization of the medical data overlaid upon the physical region of the patient's anatomy.

18. The computer program product of claim 17, wherein tracking one or more poses of a fiducial marker relative to one or more positions of an Augmented Reality (AR) headset device comprises:
- capturing one or more images via one or more cameras disposed on the AR headset device;
- calculating a first spatial transformation based on the one or more captured images and the predefined fixed reference point in 3D space; and
- generating the device pose data resulting from the spatial transformation, the device pose data representing respective physical orientations and positions of the AR headset device.

19. The computer program product of claim 18, further comprising:
- capturing one or more images of the fiducial marker via the one or more cameras disposed on the AR headset device as the AR headset device changes headset poses and as the instrument moves;
- calculating a second spatial transformation based on the one or more captured images via one or more fiducial tracking algorithms executed at the AR headset device; and
- generating respective coordinates representing one or more physical orientations and positions of the fiducial marker in the 3D space.

20. The computer program product of claim 19, further comprising:
- calculating a third spatial transformation based on a fixed distance of the instrument between the fiducial marker and the tip of the instrument; and
- generating respective coordinates representing one or more physical orientations and positions of tip of the instrument in the 3D space.

* * * * *